(12) United States Patent
McConnell et al.

(10) Patent No.: US 11,524,019 B2
(45) Date of Patent: Dec. 13, 2022

(54) SYNTHETIC COMPOSITION FOR REDUCING ALLERGY SYMPTOMS

(71) Applicant: Glycom A/S, Hørsholm (DK)

(72) Inventors: Bruce McConnell, La Tour de Peilz (CH); Louise Kristine Vigsnæs, Copenhagen (DK)

(73) Assignee: Glycom A/S, Hørsholm (DK)

( * ) Notice: Subject to any disclaimer, the term of this patent is extended or adjusted under 35 U.S.C. 154(b) by 213 days.

(21) Appl. No.: 16/640,956

(22) PCT Filed: Aug. 21, 2018

(86) PCT No.: PCT/IB2018/056308
§ 371 (c)(1),
(2) Date: Feb. 21, 2020

(87) PCT Pub. No.: WO2019/038668
PCT Pub. Date: Feb. 28, 2019

(65) Prior Publication Data
US 2020/0206250 A1  Jul. 2, 2020

(30) Foreign Application Priority Data

Aug. 21, 2017 (DK) .......................... PA 2017 00455

(51) Int. Cl.
| | |
|---|---|
| A61K 31/702 | (2006.01) |
| A61P 37/08 | (2006.01) |
| A61P 11/06 | (2006.01) |
| A61P 11/00 | (2006.01) |
| A61K 31/07 | (2006.01) |
| A61K 39/35 | (2006.01) |
| A61K 39/36 | (2006.01) |

(52) U.S. Cl.
CPC ............ *A61K 31/702* (2013.01); *A61K 31/07* (2013.01); *A61K 39/35* (2013.01); *A61K 39/36* (2013.01); *A61P 11/00* (2018.01); *A61P 11/06* (2018.01); *A61P 37/08* (2018.01)

(58) Field of Classification Search
None
See application file for complete search history.

(56) References Cited

U.S. PATENT DOCUMENTS

| 2012/0171165 A1 | 7/2012 | Buck et al. |
| 2013/0143799 A1 | 6/2013 | Knippels et al. |
| 2016/0243139 A1 | 8/2016 | Vigsnaes et al. |

FOREIGN PATENT DOCUMENTS

| EP | 2455387 A1 | 5/2012 |
| EP | 2465508 A1 | 6/2012 |
| EP | 3572087 A1 | 11/2019 |
| WO | 94/21675 A2 | 9/1994 |
| WO | 95/06728 A2 | 3/1995 |
| WO | 01/04341 A1 | 1/2001 |
| WO | 03/024998 A1 | 3/2003 |
| WO | 03/082924 A1 | 10/2003 |
| WO | 2004/047794 A2 | 6/2004 |
| WO | 2007/051476 A1 | 5/2007 |
| WO | 2007/101862 A1 | 9/2007 |
| WO | 2007/105945 A2 | 9/2007 |
| WO | 2007114683 A1 | 10/2007 |
| WO | 2009/0600743 A1 | 5/2009 |
| WO | 2010/043675 A1 | 4/2010 |
| WO | 2010/089554 A1 | 8/2010 |
| WO | 2010/115934 A1 | 10/2010 |
| WO | 2010/115935 A1 | 10/2010 |
| WO | 2011/008086 A1 | 1/2011 |
| WO | 2011/012655 A1 | 2/2011 |
| WO | 2011/100979 A1 | 8/2011 |
| WO | 2011/100980 A1 | 8/2011 |
| WO | 2011/106645 A1 | 9/2011 |
| WO | 2011/151449 A1 | 12/2011 |
| WO | 2012/007588 A9 | 1/2012 |
| WO | 2012/069415 A1 | 5/2012 |
| WO | 2012/069416 A1 | 5/2012 |
| WO | 2012/076321 A1 | 6/2012 |
| WO | 2012/076322 A1 | 6/2012 |
| WO | 2012/113404 A1 | 8/2012 |
| WO | 2012/113405 A1 | 8/2012 |
| WO | 2012/127410 A1 | 9/2012 |
| WO | 2012/140132 A1 | 10/2012 |
| WO | 2012/155916 A1 | 11/2012 |
| WO | 2012/156897 A1 | 11/2012 |
| WO | 2012/156898 A1 | 11/2012 |
| WO | 2012/175813 A1 | 12/2012 |
| WO | 2013/044928 A1 | 4/2013 |
| WO | 2013/062402 A1 | 5/2013 |
| WO | 2013/091660 A1 | 6/2013 |
| WO | 2013/139344 A1 | 9/2013 |
| WO | 2013/148134 A1 | 10/2013 |
| WO | 2015/071131 A1 | 5/2015 |
| WO | 2015/077233 A1 | 5/2015 |
| WO | 2016/046294 A1 | 3/2016 |
| WO | 2016066763 A1 | 5/2016 |
| WO | 2017/004561 A1 | 1/2017 |
| WO | 2017/129640 A1 | 8/2017 |
| WO | 2017/129642 A1 | 8/2017 |
| WO | 2017129640 A1 | 8/2017 |
| WO | 2018/006080 A1 | 1/2018 |
| WO | 2018/206434 A1 | 11/2018 |

OTHER PUBLICATIONS 18848971.0, "Extended European Search Report", EPO, dated Apr. 16, 2021, pp. 1-7.
J. Wisniewski et al., "Mechanisms of Tolerance Induction in Allergic Disease: Integrating Current and Emerging Concepts", Clin Exp Allergy, Feb. 2013; 43(2): pp. 1-21.
PCT/IB2018/056308, Notification of Transmittal of the International Search Report and the Written Opinion of the International Searching Authority, or the Declaration, dated Nov. 8, 2018, pp. 1-14.

(Continued)

*Primary Examiner* — Nora M Rooney
(74) *Attorney, Agent, or Firm* — Kunzler Bean & Adamson

(57) ABSTRACT

This invention relates to a method and composition for inducing allergen tolerance in a patient suffering from an atopic allergy or allergic asthma; hence reducing allergy symptoms in these patients.

18 Claims, No Drawings

(56) References Cited

OTHER PUBLICATIONS

L. Castillo-Courtade et al., "Attenuation of food allergy symptoms following treatment with human milk oligosaccharides in a mouse model", Allergy, vol. 70, May 2015, pp. 1091-1102.

L. Dastillo-Courtade et al., "Attenuation of food allergy symptoms following treatment with human milk oligosaccharides in a mouse model", European Journal of Allergy and Clinical Immunology, May 8, 2015, pp. 1-12.

Information From European Union Institutions, Bodies, Offices and Agencies European Commission, "Commission Notice on the classification of Food for Special Medical Purposes", Official Journal of the European Union, Nov. 25, 2017, pp. 1-15.

A. Rijnierse et al., "Food-derived oligosaccharides exhibit pharmaceutical properties", European Journal of Pharmacology, Jul. 2011, pp. S117-S123.

Xi Chen, "Human Milk Oligosaccharides (HMOS): Structure, Function, and Enzyme-Catalyzed Synthesis", Advances in Carbohydrate Chemistry and Biochemistry, vol. 72, ISSN 0065-2318, 2015, pp. 113-190.

R. Frei et al., "Microbiota and dietary interactions—an update to the hygiene hypothesis?", European Journal of Allergy and Clinical Immunology, Dec. 12, 2011, pp. 451-461.

Tadasu Urashima "Milk Oligosaccharides", Nova Biomedical, Mar. 1, 2011, pp. 99.

E. Elison et al., "Oral supplementation of healthy adults with 2!-O-fucosyllactose and lacto-N-neotetraose is well tolerated and shifts the intestinal microbiota", British Journal of Nutrition (2016), 116, Oct. 10, 2016, pp. 1356-1368.

Robert C. Edgar, "UPARSE: highly accurate OTU sequences from microbial amplicon reads", Nature Methods, vol. 10 No. 10, Oct. 2013, pp. 996-1000.

M. Haarman et al., "Quantitative Real-Time PCR Assays To Identify and Quantify Fecal Bifidobacterium Species in Infants Receiving a Prebiotic Infant Formula", Applied and Environmental Microbiology, vol. 71, No. 5, May 2005, p. 2318-2324.

A. Hevia et al., "Allergic Patients with Long-Term Asthma Display Low Levels of Bifidobacterium adolescentis", PLOS one, Feb. 3, 2016, pp. 1-11.

SYNTHETIC COMPOSITION FOR REDUCING ALLERGY SYMPTOMS

FIELD OF THE INVENTION

This invention relates to a method and composition for inducing allergen tolerance, especially long term allergen tolerance, in a patient suffering from an atopic allergy or allergic asthma; hence reducing allergy symptoms in these patients.

BACKGROUND OF THE INVENTION

The incidence of allergic diseases such as atopic dermatitis, allergic rhinitis, allergic asthma and food allergy has increased greatly over the past three decades (especially in developed countries). These conditions are among the most common chronic diseases in the world, affecting approximately 235 million people worldwide according to estimates from the World Health Organization. In the US population from 1988-1994 to 2005-2006, self reported prevalence of physician-diagnosed seasonal pollen allergy (hay fever) increased from 8.8% to 11.3%. The increasing incidence of allergic diseases as populations have become urbanised suggests that factors related to a 'western lifestyle' are driving this increase. In addition, the use of antibiotics has also been correlated with increased risk of allergic asthma. There is a significant body of evidence supporting that modification of the microbiota composition of the gastrointestinal tract that occur as a result of westernized life-style and antibiotics can disrupt mechanisms that are involved in the development of immune homeostasis and tolerance. In line with this, studies have found that long-term deficiency of fibre intake can cause great variation in the microbiota composition and alter the normal immunity, contributing to risk of developing allergic diseases and other inflammatory diseases (Frei et al. *Allergy* 67, 451 (2012).

Functionally, allergy results from an inappropriate T-helper type 2 (Th2) immune response (switching to IgE production) against generally innocuous protein. Evidence points to the link between the intestinal microbiota and Th2 responses. A recent study has demonstrated that the intestinal microbiota controls systemic Th2 responses by inducing immune homeostasis. Hence, an imbalance (dysbiosis) in the intestinal microbiota may cause impaired capacity for immune homeostasis and tolerance; increasing the risk for allergies.

A limited number of treatment options exist for atopic allergies. Certain allergy symptoms can be treated with antihistamines, corticosteroid and eicosanoid inhibitors. However these approaches only reduce symptoms and do not treat the underlying disease. Also they may have side effects. Another promising approach is allergy immunotherapy. Here the allergen, or a derivative, which causes the allergy is administered to the patient over a period of time with gradually incrementing doses. The purpose is to modify the immunological response to the allergen, resulting in long-term improvement of the patient's immune status. As such, it can be a causal or disease modifying treatment for allergies. Most patients receive at least some symptomatic relief. The mechanism of action is believed to involve induction of IgG antibodies, suppression of mast cell/basophil activity, and T cell energy. However, there is the risk that administration of the allergen which induces the allergic reaction could cause IgE mediated adverse events including anaphylactic reactions/shock. Hence recent attempts have focussed on the production of peptide fractions of the allergens which contain one or more epitopes recognised by the T cells involved in the allergic reaction. This peptide approach shows much promise but has yet to be fully evaluated.

Hence there remains a need for a safe and effective approach for providing patients who suffer from atopic allergies and/or allergic asthma with long term relief; particularly an approach which is disease modifying or effectively addresses causes.

The human intestinal microbiota is a complex and very dynamic microbial ecosystem, which is considered to serve numerous important functions for its human host, including induction of immune regulatory functions, nutrient processing and metabolic functions. The intestinal microbiota consists of various populations, which are important to preserve human health, and selective stimulation of specific intestinal bacteria to promote their growth and metabolic activity could be a helpful approach in creating a benign intestinal microbial community that is able to regulate host immune responses and induce immune homeostasis and tolerance.

Human milk oligosaccharides (HMOs) are a heterogeneous mixture of soluble glycans found in human milk. They are the third most abundant solid component after lactose and lipids in human milk and are present in concentrations of 5-25 g/l. HMOs are resistant to enzymatic hydrolysis in the small intestine and are thus largely undigested and unabsorbed. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants. Further a recent study has shown that HMOs increase the levels of bifidobacteria in healthy adults (Elison et al. *Br. J. Nutr.* 116, 1356 (2016).

WO 2015/077233 describes a method for preventing or mitigating acute allergic responses by administering at least one of an acidic and neutral HMO, but not an N-acetyl-lactosamine. An acute allergic response is defined to be an allergic condition of the immediate type. However, there is no disclosure of the treatment of atopic allergies and allergic asthma and no disclosure of the induction of long term tolerance for these conditions.

Therefore, there remains a need for a safe and effective treatment and/or preventing the occurrence of atopic allergies and/or allergic asthma which addresses underlying causes and provides in long-term relief.

SUMMARY OF THE INVENTION

A first aspect of this invention relates to a HMO for use in inducing allergen tolerance, especially long term allergen tolerance, in a patient suffering from an atopic allergy and/or allergic asthma.

A second aspect of this invention relates to
a synthetic composition comprising one or more human milk oligosaccharides and one or more of an immunotherapeutic allergen and/or an active vitamin A source, or
a synthetic composition for use in inducing allergen tolerance, especially long term allergen tolerance, in a patient suffering from an atopic allergy and/or allergic asthma, the composition comprising one or more human milk oligosaccharides.

Preferably, the synthetic composition for the use includes one or more of an immunotherapeutic allergen, and/or an active vitamin A source.

A third aspect of this invention relates to
a kit separately comprising one or more HMOs and an immunotherapeutic allergen, or
a kit for use in inducing allergen tolerance, especially long term allergen tolerance, in a patient suffering from an atopic allergy and/or allergic asthma, the kit separately comprising one or more HMOs; and an immunotherapeutic allergen.

Preferably, the kit or the kit for the use further comprises an active vitamin A source. Further, the kit or the kit for the use preferably comprises instructions for the use of the HMO and immunotherapeutic allergen in inducing allergen tolerance.

A fourth aspect of this invention relates to a method for inducing allergen tolerance, especially long term allergen tolerance, in a patient suffering from an atopic allergy and/or allergic asthma, the method comprising administering to the patient for a period of at least 7 days an effective amount of a HMO. Preferably the HMO is administered for at least 14 days; more preferably on a chronic basis until a persistent effect is obtained.

A fifth aspect of the invention relates to a method for inducing allergen tolerance, especially long term allergen tolerance, in a patient suffering from an atopic allergy and/or allergic asthma, the method comprising administering to the patient an effective amount of a HMO and optionally an immunotherapeutic allergen. The HMO and immunotherapeutic allergen can be administered together or separately. Preferably, the HMO and immunotherapeutic allergen are administered for a period of at least 7 days; for example, for at least 14 days, and more preferably on a chronic basis until a persistent effect is obtained.

A sixth aspect of the invention relates to a method for reducing allergy symptoms in a patient suffering from an atopic allergy, the method comprising administering to the patient an effective amount of a HMO and optionally one or more of an immunotherapeutic allergen, and/or an active vitamin A source.

A seventh aspect of the invention relates to a method for reducing allergy and/or asthma symptoms in a patient suffering from allergic asthma, the method comprising administering to the patient an effective amount of a HMO. The patient may also be administered one or more of an immunotherapeutic allergen, and/or an active vitamin A source.

An eighth aspect of the invention relates to a method of reducing the risk of IgE mediated adverse events during allergen specific immunotherapy utilising an immunotherapeutic allergen, the method comprising administering an effective amount of a HMO in combination with the immunotherapeutic allergen.

A ninth aspect of this invention relates to a pack for use in inducing allergen tolerance, especially long term allergen tolerance, in a patient suffering from an atopic allergy and/or allergic asthma, the pack comprising at least 7 individual daily doses of an effective amount of one or more human milk oligosaccharides.

Preferably each dose contains about 1 g to about 20 g of the human milk oligosaccharide, more preferably about 2 g to about 10 g; for example, about 3 g to about 7.5 g. Preferably, the pack comprises at least 14 individual daily doses; more preferably at least 21 daily doses; for example, at least 28 daily doses. The pack can include instructions for use.

The pack preferably further comprising at least 7 individual daily doses of one or more of an immunotherapeutic allergen and an active vitamin A source; more preferably at least 14 individual daily doses; even more preferably at least 21 daily doses; for example, at least 28 daily doses.

A tenth aspect of the invention is a use of
one or more human milk oligosaccharides (HMOs),
a synthetic composition comprising one or more human milk oligosaccharides (HMOs),
a pack comprising at least 7 individual daily doses of an effective amount of one or more human milk oligosaccharides, or
a kit separately comprising one or more HMOs and an immunotherapeutic allergen, in the dietary management of a patient suffering from an atopic allergy and/or allergic asthma.

Preferably, the immunotherapeutic allergen, in the aspects disclosed above where it is concerned, is an allergen obtained from one or more of grass pollen, tree pollen, house dust mites, cat dander, peanuts, and peptides derived from these allergens.

Preferably, the HMO, in all aspects disclosed above, is selected from 2'-FL, 3-FL, DFL, LNT, LNnT, 3'-SL, 6'-SL, LNFP-I or a mixture thereof. Preferably, the HMO comprises or consists of 2'-FL and LNnT; 2'-FL, DFL and LNnT; 2'-FL and 6'-SL; 2'-FL, DFL and 6'-SL, 2'-FL, 6'-SL and LNnT; or 2'-FL, DFL, 6'-SL and LNnT.

Preferably, the patient is a non-infant patient.

Preferably, in all aspects disclosed above, itching, fatigue and/or lack of focus or concentration is reduced in the patient.

The atopic allergy can be allergic rhinitis, atopic dermatitis, allergic conjunctivitis, rhinoconjunctivitis and/or a food allergy. Examples of food allergies include cow's milk allergy, egg allergy, peanut allergy, wheat allergy, soy allergy, fish allergy, shellfish allergy and tree nut allergy.

DETAILED DESCRIPTION OF THE INVENTION

It has now been surprisingly found that oral or enteral administration of human milk oligosaccharides to patients suffering from an atopic allergy and/or allergic asthma induces allergen tolerance, especially long term allergen tolerance, in the patient, and in consequence reduces allergy symptoms. When administered orally or enterally, human milk oligosaccharides modulate the intestinal microbiota by preferentially promoting the growth of bifidobacteria. As an outcome, a more benign intestinal microbial community is shaped and maintained, resulting in an improved gut barrier function and regulated inflammatory responses. In particular, human milk oligosaccharides when administered orally or enterally may lead to induction of tolerogenic immune cells, increased production of regulatory cytokines, and reduced mast cell degranulation.

The beneficial effect of HMOs on immune regulation and oral tolerance leading to reduction of allergic symptoms could be both direct and indirect. HMOs can directly modulate allergen-specific immune responses by supressing Th2-type reactions in atopy-prone individuals, and can stimulate the production of IL-10 (a cytokine with anti-allergic properties including inhibition of IgE-dependent mast cell activation and suppression of pro-allergic cytokines). Further, HMOs increase the abundance of bifidobacteria in the intestines. Bifidobacteria can downregulate the expression of inflammation-related genes and induce higher expression of tight junctions. This can result in a decrease in gut permeability and modulation of immune function, which helps maintaining oral tolerance. Also, bifidobacteria can promote tolerance through activation of tolerogenic phenotypes of dendritic cells leading to induction of T regulatory cell development. T regulatory cells are able to supress Th2 cells and IgE production, thus protecting against atopic allergy and/or asthma.

The beneficial effects of HMOs can also be mediated through the metabolic end products of the microbiota, such as short chain fatty acids (SCFAs; acetate, propionate and butyrate). SCFAs, produced in the intestine, are able to enter the host's circulation, where they can induce immune regulation and homeostasis. Acetate produced by bifidobacteria has immune modulatory properties by inducing proliferation and accumulation of regulatory T cells, and increasing the production of Th1 and Th17 cells. In addition, while bifidobacteria do not produce butyrate or propionate, metabolic cross-feeding on acetate or lactate by butyrate- or propionate producing bacteria takes place. Butyrate is the primary energy source for colonocytes and regulates the physical and functional integrity of the normal colonic mucosa, and protect against food allergen sensitization. Propionate protects against allergic inflammation in the lung and decreases allergic sensitization.

The following terms have the following meanings:

"Active Vitamin A source" means a source of retinal and/or retinoic acid. The active vitamin A source can be a preformed vitamin A (e.g. retinol and its esterified form, retinyl ester), a provitamin A carotenoid (e.g. beta-carotene, alpha-carotene and beta-cryptoxanthin) and the active forms of Vitamin A (for example retinal or retinoic acid).

"Allergen" means an antigen which elicits, induces, stimulates, or enhances an immune response by a cell of the immune system of a human. An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in allergic subjects.

"Allergen tolerance" means a reduced or no immune response in an individual subjected to exposure to a particular allergen. It relates to so-called desensitization immunotherapy the aim of which is to induce or restore tolerance in an allergic patient to the allergen by reducing its tendency to induce IgE production. Patients are desensitized through the administration of escalating doses of allergen that gradually decreases the IgE-dominated response. The objective of immunotherapy is to direct the immune response away from humoral immunity and toward cellular immunity, thereby encouraging the body to produce less IgE antibodies and more CD4+ T regulatory cells that secrete IL-10 and TGF-β, which skews the response away from IgE production. It also creates an increase in allergen-specific IgG4 antibodies and a decrease in allergen-specific IgE antibodies, as well as diminished mast cells and basophils, two cell types that are large contributors to allergic reaction. The phrase "long term" in the present context means that the induced tolerance to an allergen lasts for a period of at least 1 year, preferably longer than 1 year, such as 2-5 years or longer.

"Allergic asthma" means asthma which is triggered by inhaling an allergen. It is associated with a past history and/or family history of allergic disease such as eczema, allergic rhinitis, or food allergy.

"Asthma" an inflammatory disease of the airways of the lungs characterised by variable and recurring symptoms, reversible airflow obstruction, and bronchospasm. Symptoms include episodes of wheezing, coughing, chest tightness, and shortness of breath.

"Atopic allergy" means a form of allergy that afflicts persons hypersensitive to certain allergens. Examples include allergic rhinitis, atopic dermatitis, allergic conjunctivitis and food allergies such as cow's milk allergy, egg allergy, peanut allergy, wheat allergy, soy allergy, fish allergy, shellfish allergy and tree nut allergy. Atopic allergies show a strong hereditary component. Symptoms include swelling of the nasal mucosa, runny nose, sneezing, red eyes, an itchy rash, abdominal pain, bloating, vomiting, diarrhoea, and the like.

Dietary management" means exclusive or partial feeding of patients who, because of a disease, disorder or medical condition are suffering from:
  either have a limited, impaired or disturbed capacity to take, digest, absorb, metabolise or excrete ordinary food or certain nutrients contained therein, or metabolites, or
  have other medically-determined nutrient requirements (see: Commission Notice on the classification of Food for Special Medical Purposes of the European Commission, *Official Journal of the European Union C* 401, 25.11.2017, p. 10-11).

"Effective amount" means an amount of an HMO sufficient to render a desired treatment outcome. An effective amount can be administered in one or more doses to achieve the desired treatment outcome. In one embodiment, the desired treatment outcome is a persistent effect.

"Enteral administration" means a form for delivery of a composition that causes the deposition of the composition in the gastrointestinal tract (including the stomach). Methods of enteral administration include feeding through a nasogastric tube or jejunum tube, oral, sublingual and rectal.

"Human milk oligosaccharide" or "HMO" means a complex carbohydrate found in human breast milk (Urashima et al.: Milk Oligosaccharides. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyl-lactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI) lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Immunotherapeutic allergen" means an allergen which causes the allergy in the patient, or a protein or peptide derivative of the allergy which elicits an immune response. Typically, they are obtained from one or more of grass pollen, tree pollen, house dust mites, cat dander, peanuts, egg, shellfish, nuts, and peptides derived from these allergens. Suitable immunotherapeutic allergens are described in WO 94/21675, WO 95/06728, WO 2003/024998, WO 2003/082924, WO 2010/089554, WO 2011/106645, WO 2011/151449 and WO 2017/004561.

"Microbiota", "microflora" and "microbiome" mean a community of living microorganisms that typically inhabits a bodily organ or part, particularly the gastro-intestinal organs. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucous layer covering the epithelium of the gastrointestinal tract, and luminal-associated microbiota, which is found in the lumen of the gastrointestinal tract.

"Non-infant human" or "non-infant" means a human of 3 years of age and older. A non-infant human can be a child, an adolescent, an adult or an elderly person.

"Oral administration" means a form for the delivery of a composition through the mouth. Accordingly, oral administration is a form of enteral administration.

"Persistent effect" means that one or more clinically relevant symptoms of the immune response is reduced post treatment in the patient when exposed to an allergen as compared to before the subject is administered the first dose. A persistent effect may be evaluated at least two months after the subject has stopped treatment, such as after at least three, four, five, six, nine or twelve months. For example, the symptoms may be reduced during two to three treatment years.

"Relative abundance of bifidobacteria" means the abundance of bifidobacteria relative to other genus in the microbiota of the gastro-intestinal tract.

"Relative growth of bifidobacteria" means the growth of bifidobacteria relative to other genus in the microbiota in the gastro-intestinal tract.

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition may be identical with a naturally occurring composition.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

In accordance with this invention, it has been discovered that an HMO can induce allergen tolerance, especially long term allergen tolerance, and consequently symptom relief in patients suffering from an atopic allergy or allergic asthma. The HMO can be combined with an immunotherapeutic allergen, and/or an active vitamin A source such as vitamin A and retinoic acid. The HMO can also increase the abundance, particularly the relative abundance, of bifidobacteria, in the microbiota in the gastro-intestinal tract of the patient.

The HMO can be a neutral HMO or an acidic HMO, or a mixture of both. The neutral HMO is, in one embodiment, one or more fucosylated HMOs; in another embodiment, the HMO is one or more non-fucosylated HMOs. In one embodiment, the neutral HMO is a mixture of neutral HMOs, preferably a mixture comprising or consisting of a fucosylated and a non-fucosylated neutral HMO. Particularly, the mixture contains, consists or consists essentially of one or more fucosylated neutral HMO selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, preferably, at least 2'-FL, and a non-fucosylated neutral HMO selected from the list consisting of LNT, LNnT, LNH, LNnH, pLNH and pLNnH, e.g. LNnT. In some preferred embodiment, the mixture contains, consists or consists essentially of a fucosylated neutral HMO selected from the list consisting of 2'-FL, 3-FL and DFL, and a non-fucosylated neutral HMO selected from the list consisting of LNT and LNnT, advantageously the mixture comprises, consists or consists essentially of i) 2'-FL and/or DFL and ii) LNnT and/or LNT (meaning that the mixture comprises, consists or consists essentially of at least one of 2'-FL and DFL, and at least one of LNnT and LNT, for example a mixture comprising, consisting or consisting essentially of 2'-FL and LNnT; or 2'-FL, DFL and LNnT). The mixture can also be that containing, consisting or consisting essentially of 2'-FL and DFL. In another embodiments, the acidic HMOs are preferably selected from 3'-SL and 6'-SL. Exemplary HMO mixtures containing an acidic HMO are those comprising, consisting or consisting essentially of 2'-FL and 6'-SL; 2'-FL, DFL and 6'-SL, 2'-FL, 6'-SL and LNnT; or 2'-FL, DFL, 6'-SL and LNnT.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antihistamines, eicosanoids, and anti-inflammatory agents. Preferably the pharmaceutical composition comprises one or more of an immunotherapeutic allergen and an active vitamin A source (e.g. retinoic acid).

An effective dosage of these compositions for a human can be determined in a conventional manner, based upon factors such symptom status, body weight and age. In some cases, the dosage will be at a concentration similar to that found for the HMO in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Doses in the range of 3 g to 7 g per day are preferred. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). The lipid can be a mixture of MCTs and LCTs. For example, MCTs can comprise about 30% to about 70% by weight of the lipids, more specifically about 50% to about 60% by weight. MCTs offer the advantage of easier digestion which can be important for patients with inflamed GI tracts. Generally the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for patients having inflammatory conditions. Omega-3 fatty acids are preferred due to their anti-inflammatory properties.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. B. animalis subsp. lactis BB-12, B. lactis HN019, B. lactis Bi07, B. infantis ATCC 15697, L. rhamnosus GG, L. rhamnosus HNOOI, L. acidophilus LA-5, L. acidophilus NCFM, L. fermentum CECT5716, B. longum BB536, B. longum AH1205, B. longum AH1206, B. breve M-16V, L. reuteri ATCC 55730, L. reuteri ATCC PTA-6485, L. reuteri DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a non-infant via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition can also be in a nutritional unit dosage form such as a capsule, tablet or sachet. For example, the synthetic composition can be in a tablet form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethylcellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("QoQIO") and glutathione.

The unit dosage forms, especially those in sachet form, can also include various nutrients including macronutrients.

For inducing allergen tolerance, especially long term allergen tolerance, in a patient suffering from an atopic allergy or allergic asthma, the amount of HMO(s) required to be administered will vary depending upon factors such as the risk and severity of the allergy or asthma, age, the form of the composition, and other medications being administered. However, the required amount can be readily set by a medical practitioner and would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Doses in the range of 3 g to 7 g per day are preferred. Appropriate dose regimes can be determined by conventional methods. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

The HMO or synthetic composition can be presented in the form of a pack comprising at least 7 individual daily doses of an effective amount of the human milk oligosaccharide. The daily doses are preferably in sachet/stick pack form but may be in any suitable form. Each dose preferably contains about 1 g to about 20 g of the human milk oligosaccharide, more preferably about 2 g to about 10 g, for example about 3 g to about 7.5 g. Preferably, the pack comprises at least 14 daily doses; more preferably at least 21 daily doses. The pack can include instructions for use.

The invention also relates to a method for inducing allergen tolerance, especially long term allergen tolerance, comprising administering to the patient an effective amount of a HMO and an immunotherapeutic allergen. The HMO and immunotherapeutic allergen can be administered together in a single composition or separately. If administered in a single composition, the compositions described above can be used or sublingual compositions (for example in the form of a tablet, capsule, lozenge, or caplet) as described in WO 2004/77994 and WO 2007/051476 can be used. If administered separately, the HMO can be formulated into the compositions described above. The immunotherapeutic allergen can be formulated into any suitable form for enteral or parenteral administration. Preferably the immunotherapeutic allergen is formulated into a sublingual composition (for example as described in WO 2004/77994 and WO 2007/051476) or a liquid injectable composition as described in WO 2010/043675. If administered separately, the HMO and immunotherapeutic allergen are preferably combined into a single package or kit with instructions for the co-administration of the HMO and immunotherapeutic allergen.

The invention also relates to a method for reducing allergy symptoms comprising administering to the patient an effective amount of a HMO and one or more of an immunotherapeutic allergen and an active Vitamin A source. The HMO and immunotherapeutic allergen and/or Vitamin A source can be administered together in a single composition or separately as described above.

The invention also relates to a method for reducing allergic asthma symptoms comprising administering to the patient an effective amount of a HMO. The patient may also be administered one or more of an immunotherapeutic allergen and an active Vitamin A source. The HMO and immunotherapeutic allergen and/or Vitamin A source can be administered together in a single composition or separately as described above.

Vitamin A is a group of fat-soluble retinoids, including retinol, retinal, and retinyl esters. Two forms of vitamin A are generally available for use in the human diet; namely preformed vitamin A (e.g. retinol and its esterified form, retinyl ester) and provitamin A carotenoids. The most important provitamin A carotenoid is beta-carotene; other provitamin A carotenoids are alpha-carotene and beta-cryptoxanthin. The vitamin A may also be provided as an active derivative of Vitamin A; include retinal and retinoic acid.

The active vitamin A source may be formulated into composition along with the HMO or into a composition with the immunotherapeutic allergen.

The invention also relates to a method of reducing the risk of IgE mediated adverse events during allergen specific immunotherapy utilising an immunotherapeutic allergen, the method comprising administering an effective amount of a HMO in combination with the immunotherapeutic allergen. The HMO and immunotherapeutic allergen can be administered together in a single composition or separately as described above.

When an HMO and an immunotherapeutic allergen are used, they are administered for a period of at least 7 days; preferably for at least 14 days; for example, for at least 3 months. The HMO and an immunotherapeutic allergen can be administered over extended periods on a chronic basis until a persistent post treatment effect is obtained; for example for more than 1 year.

The immunotherapeutic allergen can be administered in clinically relevant doses, such as therapeutically sufficient doses. For example, a single dose of each allergen may be in the range of 1 to 1000 nanomole, for example 1 to 500 nanomole, for example 1 to 250 nanomole, for example 5 to 250 nanomole. The single dose may be repeated once daily, weekly, biweekly or monthly or quarterly.

The immunotherapeutic allergen can be dosed in a regimen usually applied in the field of allergy immunotherapy. For example, immunotherapeutic allergen can be administered as a single dose with daily, weekly, bi-weekly, monthly or quarterly intervals over a period of at least 2-6 months or even longer until a more persistent effect is achieved. When in the form of drops or injectables, it is also envisaged that the treatment is initiated by an up-dosing phase with the allergen being administered in increasing doses within one day or with daily, weekly or bi-weekly intervals until the target maintenance dose is achieved.

The immunotherapeutic allergen can be any allergen which induces an allergic response, for example a grass allergen, a cat dander allergen, house mite dust allergen, peanut allergen, and the like.

Whilst the invention has been described with reference to a preferred embodiment, it will be appreciated that various modifications are possible within the scope of the invention.

EXAMPLES

Example 1

Thirty four-week-old female C3H/HeJ mice are individually housed to avoid contamination between mice. Prior to the experiment, the mice are randomly assigned to three groups, ten mice in each group. Two of the groups (Group 1 and Group 2) are fed an Ovalbumin (OVA) free chow diet and one group (Group 3) is fed an OVA free chow diet containing 5% of HMOs (2'-FL and LNnT, mass ratio 4:1). Fresh water is administered daily and all mice have free access to drinking water. After two weeks, the mice are oral sensitized by intragastric administration of 50 mg of OVA with 10 µg of cholera toxin (CT). The mice are sensitized once weekly for 6 weeks. The mice in Group 1 and Group 3 are gavaged with 0.2 ml of phosphate-buffer saline solution (PBS, pH 7.2) containing OVA and CT, and the mice in group 2 are gavaged with PBS without OVA and CT as a negative control.

Fresh faecal samples are collected at day 0, 14, 28, 56. Samples are immediately frozen and stored at −80° C. until further analysis.

To determine serum antibody responses and SCFAs levels, tail-vein blood is collected weekly starting just before the initial sensitization. Sera are immediately frozen and stored at −80° C. until further analysis.

To assess levels of serum IgE, the enzyme-linked immunosorbent assay (ELISA) is used. Briefly, NUNC MaxiSorp 96-well plates are coated with 2 µg/ml goat anti-mouse IgE overnight at 4° C. Samples are added the next day and incubated overnight at 4° C. before the addition of a 1 µg/ml final concentration of alkaline phosphatase-conjugated goat anti-mouse IgE. 4-nitrophenyl phosphate sodium salt hexahydrate (pNPP) is used as a substrate, and the colorimetric reaction is read at 405 nm on a microplate reader.

After six weeks, the mice are euthanized by cervical dislocation, and the ear and small intestine are dissected for histological analysis. Tissues are fixed in 10% formalin in PBS, embedded in paraffin, and cut into 3-5 µm thick sections. The sections are stained with hematoxylineosin for general analysis, with toluidine blue for mast cell evaluation, or with Luna's method for eosinophil granule identification.

Caecum (full and empty) are precisely dissected, weighed, immersed in liquid nitrogen and stored at −80° C., for further analysis.

Allergic symptoms are evaluated after the mice are euthanized, utilizing a scoring system: 0, no symptoms; 1, puffiness of the tail; 2, 1-3 scabs on the tail; 3, 4-6 scabs on the tail; 4, 7-9 scabs on the tail; 5, more than 9 scabs on the tail; 6, 1-2 blood stains and more than 9 scabs on the tail; 7, more than 2 blood stains and more than 9 scabs on the tail.

To assess the microbiota profile, DNA is extracted from faecal samples and caecum contents using QIAamp DNA Stool Mini Kit. The DNA concentration of extracts is measured using NanoDrop. PCR is done with the forward primer S-D-Bact-0341-b-S-17 and reverse primer S-D-Bact-0785-a-A-21 (46) with Illumina adapters attached. These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013) is used for bioinformatical analysis of the sequence data.

The levels of SOFA in caecum content and serum are analysed using HPLC Ultimate 3000 (Dionex, Sunnyvale, Calif.) equipped with an U3000 RS diode array detector (Dionex).

The results show that oral ingestion of HMOs protects against allergen sensitization by significantly lowering the level of serum IgE, and decreasing the levels of degranulated mast cells, eosinophil, and tail scabs. Additionally, ingestion of HMOs inhibits the emergence of microbiota dysbiosis associated with allergy, by modulating the intestinal microbiota, and increasing the abundance of bifidobacteria. The level of SCFA correlates negatively with IgE levels and tail scabs. Collectively, HMOs are able to prevent allergen hypersensitivity, and suppress allergy symptoms.

Example 2

A human study to assess the effect of HMO on atopic allergy is carried out. One hundred and twenty-six patients are screened for the study. Each patient answers an electronic, base-line questionnaire containing questions on allergy symptoms and symptoms of abdominal pain, diarrhoea, constipation, and bloating. The symptoms are assessed on a 5 point Likert scale where a score of 1 indicates no symptoms and a score of 5 indicates severe symptoms. Twenty-six patients with active allergy symptoms are recruited into the study (symptoms scores of 2 and above).

Each recruited patient is then administered 5 g of a 4:1 mix (by weight) of 2'-FL and LNnT on a daily basis for a period of 3 weeks. The patient then answers an electronic, follow up questionnaire containing questions on allergy symptoms and symptoms of abdominal pain, diarrhoea, constipation, and bloating. Again, the symptoms are assessed on a 5 point Likert scale.

The patients experience a significant decrease in overall allergy symptoms compared to baseline ($p<0.0001$ tested using the Wilcoxon matched-pairs signed rank test). The mean overall allergy symptom decrease is 36%. The patients also experience significant decrease in abdominal pain and bloating.

Example 3

A human study to assess the effect of HMO on atopic allergy is carried out. Seven hundred and fifty patients are screened for the study. Each patient answers an electronic, base-line questionnaire containing questions on allergy symptoms and symptoms of abdominal pain, diarrhoea, constipation, and bloating. The symptoms are assessed on a 5 point Likert scale where a score of 1 indicates no symptoms and a score of 5 indicates severe symptoms. One hundred and eighty three patients with active allergy symptoms are recruited into the study (symptoms scores of 2 and above).

Each recruited patient is administered 5 g of either 2'-FL alone or a 4:1 mix (by weight) of 2'-FL and LNnT on a daily basis for a period of 12 weeks. The patient then answers an electronic, follow up questionnaire containing questions on allergy symptoms, itching and symptoms of abdominal pain, diarrhoea, constipation, bloating and fatigue. Again, the symptoms are assessed on a 5 point Likert scale.

The mean scores over the 12 weeks for overall allergy symptoms, itching, abdominal pain and fatigue are as those in the following table:

| Time | Allergy symptom score | Itching symptom score | Abdominal pain symptom score | Fatigue symptom score |
|---|---|---|---|---|
| Baseline | 2.8 | 2.7 | 2.7 | 3.3 |
| 3 weeks | 1.8 | 2.0 | 1.8 | 1.9 |
| 6 weeks | 1.8 | 1.8 | 1.8 | 2.0 |
| 9 weeks | 1.7 | 1.7 | 1.8 | 2.0 |
| 12 weeks | 1.5 | 1.5 | 1.7 | 2.0 |

The patients experience a significant decrease in overall allergy symptoms and itching symptoms compared to baseline ($p<0.001$ tested using the Wilcoxon matched-pairs signed rank test). The mean allergy symptom decrease is 46%. The patients also experience significant decrease in abdominal pain and fatigue. Allergic asthma patients experience a reduction in overall asthma symptoms scores.

Patients completing 12 weeks are offered an opportunity to remain in the program. After 21 weeks, patients continue to report improved tolerance and reduced overall allergy symptoms.

The invention claimed is:
1. A method comprising:
 selecting an adult human with allergic asthma;
 selecting an effective amount of a composition consisting of human milk oligosaccharides (HMO) in a mixture consisting of 2'-fucosylactose (2'-FL) and lacto-N-neotetraose (LNnT) with a mass ratio 2'-FL:LNnT of from 4:1 to 2:1, the selected amount effective for increasing the relative abundance of *Bifidobacterium adolescentis* in the gut microbiota of the adult human; and
 increasing in the gut microbiota of the adult human the relative abundance of *Bifidobacterium adolescentis* in the gut microbiota of the adult human and reducing the severity of one or more symptoms of the allergic asthma by administering the selected effective amount of the composition for an initial treatment phase of at least fourteen days.

2. The method of claim 1, wherein reducing the severity one or more symptoms of allergic asthma comprises reducing one or more symptoms selected from reversible airflow obstruction, bronchospasm, wheezing, coughing, chest tightness, shortness of breath and combinations thereof.

3. The method of claim 1, wherein the adult human with allergic asthma is undergoing immunotherapeutic allergen treatment.

4. The method of claim 3, further comprising enhancing the effectiveness of the immunotherapeutic allergen for inducing allergen tolerance by administering the selected effective amount of the mixture of 2'-FL and LNnT.

5. The method of claim 1, wherein an initial dosage of the mixture of 2'-FL and LNnT administered during the initial treatment phase is from 5 g to 10 g per day.

6. The method of claim 5, further comprising administering to the adult human a maintenance dosage of the mixture of 2'-FL and LNnT of from 1 g to 2.5 g per day during a maintenance phase that follows the initial treatment phase.

7. The method of claim 1, further comprising reducing immunoglobulin E (IgE) serum levels in the adult human by administering the selected effective amount of the HMOs mixture of 2'-FL and LNnT.

8. A method comprising:
 selecting an adult human with allergic asthma;
 selecting an effective amount of a composition consisting of human milk oligosaccharides (HMO) in a mixture consisting of 2'-fucosylactose (2'-FL), difucosyllactose (DFL), and lacto-N-neotetraose (LNnT), the amount effective for increasing the relative abundance of *Bifidobacterium adolescentis* in the gut microbiota of the adult human; and
 increasing the relative abundance of *Bifidobacterium adolescentis* in the gut microbiota of the adult human and reducing the severity of one or more symptoms of the allergic asthma by administering the selected effective amount of the composition for an initial treatment phase of at least fourteen days.

9. The method of claim 8, wherein the adult human with allergic asthma has a family history of having one or more atopic allergies selected from allergic rhinitis, allergic dermatitis, or a combination thereof.

10. The method of claim 8, wherein the adult human with allergic asthma is undergoing immunotherapeutic allergen treatment.

11. The method of claim 10, wherein the immunotherapeutic allergen is selected from a grass pollen allergen, a house mite dust allergen, a cat dander allergen, a tree pollen allergen, an egg allergen, a shellfish allergen, a peanut allergen, or combinations thereof.

12. The method of claim 8, wherein an initial dosage of the mixture of 2'-FL and LNnT administered during the initial treatment phase is from 5 g to 10 g per day.

13. The method of claim 12, further comprising administering to the adult human a maintenance dosage of the mixture of 2'-FL and LNnT of from 1 g to 2.5 g per day during a maintenance phase that follows the initial treatment phase.

14. The method of claim 8, wherein reducing the one or more symptoms of the allergic asthma comprises reducing one or more symptoms selected from reversible airflow obstruction, bronchospasm, wheezing, coughing, chest tightness, shortness of breath, itching, fatigue, and combinations thereof.

15. A method comprising:
 selecting an adult asthma patient with allergic asthma;
 selecting an effective amount of a composition consisting of one or more human milk oligosaccharides (HMOs) chosen from the group consisting of 2'-fucosylactose ("2'-FL"), difucosyllactose ("DFL"), lacto-N-tetraose ("LNT"), lacto-N-neotetraose ("LNnT"), and combinations thereof, the one or more HMOs effective for modulating the gut microbiota of the adult asthma patient by increasing the relative abundance of *Bifidobacterium adolescentis* in the gut microbiota of the adult asthma patient; and
 increasing the relative abundance increasing the relative abundance of *Bifidobacterium adolescentis* in the gut microbiota of the adult asthma patient and reducing levels of one or more components of allergic inflammation in the adult asthma patient by administering during an initial treatment phase of at least fourteen days, the selected effective amount of the chosen one or more synthetic neutral human milk oligosaccharides ("HMOs").

16. The method of claim 15, wherein the one or more components of allergic inflammation with levels reduced in the adult asthma patient by administering the selected amounts of the chosen one or more synthetic neutral HMOS are selected from the group consisting of immunoglobulin E (IgE), degranulated mast cells, and eosinophils.

17. The method of claim 15, wherein an initial total dosage of the one or more synthetic neutral HMOs administered during the initial treatment phase is from 5 g to 10 g per day.

18. The method of claim 17, further comprising administering to the adult human a maintenance dosage of the selected one or more HMOs of from 1 g to 2.5 g per day during a maintenance phase that follows the initial treatment phase.

* * * * *